US00PP25299P2

(12) United States Plant Patent
Beckman et al.

(10) Patent No.: US PP25,299 P2
(45) Date of Patent: Feb. 24, 2015

(54) PEACH TREE NAMED 'GULFSNOW'

(50) Latin Name: ***Prunus Persica* (L.) Batsch.**
Varietal Denomination: Gulfsnow

(75) Inventors: Thomas G. Beckman, Warner Robins, GA (US); Jose X. Chaparro, Gainesville, FL (US); Patrick J. Conner, Tifton, GA (US)

(73) Assignees: The United States of America, as represented by the Secretary of Agriculture, Washington, DC (US); Flordia Foundation Seed Producers, Greenwood, FL (US); University of Georgia Research Foundation, Athens, GA (US)

( * ) Notice: Subject to any disclaimer, the term of this patent is extended or adjusted under 35 U.S.C. 154(b) by 43 days.

(21) Appl. No.: 13/573,438

(22) Filed: Sep. 14, 2012

(51) Int. Cl.
*A01H 5/00* (2006.01)

(52) U.S. Cl.
USPC ..... Plt./195

(58) Field of Classification Search
CPC .. A01H 5/0868; A01H 5/0856; A01H 5/0837
USPC ..... Plt./195
See application file for complete search history.

(56) References Cited

U.S. PATENT DOCUMENTS

| | | | |
|---|---|---|---|
| PP5,251 | P | 6/1984 | Doyle |
| PP10,175 | P | 1/1998 | Zaiger et al. |
| PP17,911 | P3 | 8/2007 | Clark et al. |
| PP20,174 | P2 | 7/2009 | Chaparro et al. |
| PP21,837 | P2 | 4/2011 | Chaparro et al. |

*Primary Examiner* — Kent L Bell
(74) *Attorney, Agent, or Firm* — Gail E. Poulos; John D. Fado; Lesley Shaw

(57) ABSTRACT

A new and distinct variety of peach tree, denominated 'Gulfsnow', has a winter chilling requirement estimated at 400 chill units (cu). The tree is medium size, moderately vigorous, and semi-upright in growth habit. It bears showy, pink flowers, and leaves with globose glands. Trees of 'Gulfsnow' are self-fertile and regularly bear annual crops of early season fruit that are large size (185 g) for its ripening season. Fruit are uniformly firm with non-melting white flesh. Fruit are nearly round, and uniform with substantially symmetrical shape, and have an attractive 50 to 60% red skin. The fruit of 'Gulfsnow' usually ripen 10 days after 'Gulfcrimson' peach in early June at Attapulgus, Ga.

1 Drawing Sheet

Latin name of the genus and species of the plant claimed: 'GULFSNOW' is a new peach tree that is a *Prunus persica* (L.) Batsch.

Variety denomination: The new peach tree claimed is of the variety denominated 'GULFSNOW', *Prunus persica* (L.) Batsch.

BACKGROUND OF THE INVENTION

The present invention relates to the discovery of a new and distinct variety of peach tree, botanically known as *Prunus persica* (L.) Batsch, and herein referred to as 'Gulfsnow', as herein described and illustrated. This new and distinct variety of peach [*Prunus persica* (L.) Batsch] tree is adapted to a subtropical (moderate chill) winter climate. This new tree, named 'Gulfsnow', produces well colored, good eating quality, white and non-melting flesh fruit for fresh market in early June at Attapulgus, Ga. Contrast is made to 'Gulfcrimson' peach (U.S. Plant Pat. No. 20,174; herein incorporated by reference in its entirety), a standard variety, for reliable description. 'Gulfsnow' is a promising candidate for commercial success in that it has attractive, sweet, white-fleshed fruit that ripen evenly.

The new and distinct variety of peach tree 'Gulfsnow' originated in a cultivated area of the fruit breeding program located at Attapulgus, Ga. where it was tested. 'Gulfsnow' resulted from a cross of AP98-30×AP99-20W selections. Both parents are selections of complex origin from this breeding program. 'Gulfsnow' was selected in 2006 because it exhibited white, non-melting flesh, in a large size fruit with a bright red . It was designated and tested as AP06-09W. It was asexually propagated by budding onto 'Flordaguard' (unpatented) seedling rootstock (for root-knot nematode control) and determined to have unique tree and fruit characteristics making it worthy for commercial fresh fruit production. There are no known effects of this standard rootstock on this scion cultivar. Asexually propagated plants remained true to the original tree and all characteristics of the tree and the fruit have transmitted for 2 generations.

'Gulfsnow' peach tree is a new and distinct variety that bears white, non-melting flesh fruit of good flavor, brix, and eating quality, that ripens in early June at Attapulgus (Table 1). 'Gulfsnow' blooms in mid-late February at Attapulgus typically between 'Flordaking' peach (350 chill units) and 'Sunlite' nectarine (450 chill units). Thus, the chilling requirement is estimated at 400 chill units. The trees are vigorous, productive and without alternate bearing. Tree growth of two meters in height and one and half meter in width is typical the first growing season in the field at Attapulgus. Terminal growth of up to a half meter annually is common on mature 5-year-old trees with normal pruning to a vase shape. 'Gulfsnow' can be clearly distinguished from either of its parents. 'Gulfsnow' differs from its seed parent, AP98-30, in that 'Gulfsnow' has a notably lower chilling requirement (approximately 400 Cu) than does AP-98-30 (500 cu). 'Gulfsnow' has a shorter fruit development period from bloom to ripe, i.e. averaging approximately 109 days vs. approximately 123 for AP98-30 and 'Gulfsnow' ripens approximately 18 days before AP98-30. 'Gulfsnow' is white fleshed while AP98-30 is yellow fleshed. 'Gulfsnow' differs from it pollen parent, AP99-20W, in that 'Gulfsnow' has a notably higher chilling requirement (approximately 400 cu) than does AP-99-20W (approximately 300 cu). 'Gulfsnow' has a longer fruit development periods, i.e., averaging 109 says vs. 98 days for A99-20W and 'Gulfsnow' ripens approximately 17 days after AP99-20W. 'Gulfsnow' has globose leaf glands while AP99-20W has reniform glands.

The first fruit ripen the first week of June at Attapulgus or in about 110 days from full bloom, ca. 10 days after 'Gulfcrimson' ripening. The fruit are uniformly large size, averaging 185 g when properly thinned to a full crop. However, 'Gulfsnow' fruit are more round than 'Gulfcrimson' which has a longer fruit. Ripe fruit have averaged 53% red blush. There is some red pigment in the flesh but none in the flesh at the pit. The flower anthers are deep yellow, and leaf glands are globose, common characteristics of many standard peach varieties. No buttons (parthenocarpy fruit) or split pits have been observed.

TABLE 1

Tree performance and fruit characteristics[z] of 'Gulfsnow' and Gulfcrimson' (Attapulgus, Ga., 2006-2012).

| | Tree | | | Fruit | | |
|---|---|---|---|---|---|---|
| Cultivar | Bloom (Jul) | Crop (%) | Harv. (Jul) | Diam. (mm) | Wt. (gm) | Shape |
| Gulfsnow | 47 | 40 | 158 | 71 | 185 | 8 |
| Gulfcrimson | 52 | 77 | 148 | 69 | 163 | 7 |
| Sig. (P)[y] | 0.36 | 0.12 | 0.01 | 0.32 | 0.15 | 0.10 |

| | Fruit | | | | |
|---|---|---|---|---|---|
| Cultivar | Red (%) | Attr. | Qual. | Firm. | Brix (%) |
| Gulfsnow | 53 | 8 | 7 | 8 | 11 |
| Gulfcrimson | 80 | 8 | 7 | 8 | 10 |
| Sig. (P)[y] | .0001 | 0.17 | 1.00 | 1.00 | 0.13 |

[z]Subjective Shape, Attractiveness (Attr.), Quality (Qual.) and Firmness (Firm.) ratings: 1 = least desirable, 7 = commercially acceptable, 10 = most desirable.
[y]Significance (P) of difference of means in each column, F-test. Percent Crop Load (Crop), Red Skin Color (Red) and Soluble Solids (Brix) data were transformed as arcsine (square root) prior to analysis (Gomez and Gomez, 1984). Untransformed means presented. Data analyzed by General Linear Models (GLM) program of the Statistical Analysis System for personal computers (SAS, 2003). Years were treated as blocks.

The new variety has been named 'Gulfsnow'.

BRIEF DESCRIPTION OF THE PHOTOGRAPHS

FIG. 1 is a color photograph which shows a typical specimen of the fruit, leaf, and stem of the new variety as nearly true as it is reasonably possible to make in a color illustration of this type. The photograph shows an attractive shape and exterior coloration of 4 specimens of fruit above a ruler in side view, stem end view, a side view showing the suture and a fruit cut longitudinally to show the flesh and pit.

DETAILED DESCRIPTION OF THE NEW CULTIVAR

The following is a detailed description of the botanical and pomological characteristics of the subject peach tree. Color data (except those in common terms) are described from "The Pantone Book of Color", published by H. N. Abrams, Inc., N.Y. 1990.

Where dimensions, sizes, colors and other characteristics are given, it is to be understood that such characteristics are approximations of averages set forth as accurately as practicable.

The tree, flowers, and fruit of 'Gulfsnow' may vary in slight detail due to variations in soil type, cultural practices, and climatic condition. The potential for commercial production of fresh fruit is high, due to its attractive red over a creamy white ground color, large size fruit of good flavor, and good firmness with even ripening throughout the fruit. The present botanical description is that of the variety grown on 5-year-old trees on 'Flordaguard' rootstock under the ecological conditions at Attapulgus, Ga.

Tree:

*Size*.—Trees are medium stature when trained to an open vase form.

*Height*.—Trees typically attain a height of approximately 3.0 m and spread of approximately 5.6 m after 8 growing seasons with annual dormant pruning.

*Vigor*.—Moderately vigorous, and must be summer and winter pruned when grown to a vase shape to keep the tree open to get strong fruiting wood in the lower center. Trees respond typically to irrigation and fertilization. Tree growth of two meters in height and one and half meter in width is typical the first growing season in the field at Attapulgus.

*Density*.—Light to medium in branching habit. Pruning is required to open the tree center to promote sunlight entrance for enhancing fruit color and sugar.

*Form*.—Semi-upright, but easily pruned to vase shape.

*Hardiness*.—Hardy with respect to typical south Georgia winters.

*Bearer*.—Productive annually without alternate bearing observed. Trees are self fertile and should be fruit thinned to avoid limb breakage and obtain large fruit size.

*Chilling requirement*.—Estimated endodormancy chilling requirement is 400 chill units based on time of bloom and leafing in relation to standard varieties.

Trunk:

*Size*.—Medium trunk diameter attaining 14 cm diameter at a height of 30 cm at the end of 5 years growth at Attapulgus.

*Texture*.—Medium smooth, even as tree ages.

*Bark color*.—Older bark gray, Chinchilla (Pantone 17-1109).

*Lenticels*.—Moderate number (8 to 10 per 4 square inches of surface area of trunk) and large (15 to 22 mm length, perpendicular to the trunk), gray, Lead Gray (Pantone 17-1118) with the center being yellowish brown, Honey Gold (Pantone 15-1142).

Branches:

*Size*.—Strong growth of scaffold branches. Fruiting branches are mostly large diameter (4 to 6 mm) and not overly twiggy, resulting in strong fruiting wood. Thus, the tree growth and structure permits easier and faster winter pruning.

*Texture*.—Relatively smooth, medium size lenticels shorter than found on trunk and old scaffolds. .

*Color*.—New wood is light green, Celery Green (Pantone 13-0532); Old wood is brown, Macaroon (Pantone 16-1323).

*Crotch angles*.—Angles are selected at 45 to near 90 degrees in first year of tree training. Natural angles are within the normal range of standard varieties for a semi-upright tree which is slightly more upright than 'Gulfcrimson'.

Leaves:

*Size*.—Medium; 15 to 17 cm length, including the petiole; 34 to 38 mm width. Measurements were made on vigorous upright shoots of summer growth.

*Thickness*.—Regular and average for commercial peach varieties. Not noticeably unusual.

*Form*.—Lanceolate.

*Apex*.—Acute.

*Margin*.—Serrulate, slightly undulate.

*Base*.—Cuneate.

*Surface*.—Upper, glabrous; Lower, medium large veins that are pinnately netted.

*Color*.—Lower surface is green, Spinach Green (Pantone 16-0439); Upper surface is slightly darker green, Forest Green (Pantone 17-0230).

*Glands*.—Usually 2, globose glands on lower leaf blade. Leaf glands on young leaves are light green, Leek Green (Pantone 15-0628). Size averages less than 1 mm in diameter.

*Petiole*.—Average 8 mm length; 1.5 mm diameter. Light green, Water Lily (Pantone 11-0304) on older leaves of summer. Shape is grooved longitudinally.

*Stipules*.—Medium (equal to most commercial peach varieties), usually 2 per bud, and abscising just before leaf becomes full size in summer growth. Color at full size is Spinach Green (Pantone 16-0439), but tinged red, Dry Rose (Pantone 18-1725) from base upward before abscising.

*Arrangement*.—Alternate.

Flower buds:

*Hardiness*.—Hardy with respect to south Georgia winters.

*Abundance*.—Very high due to shorter than average internode length. Most buds set fruit in absence of spring frosts and show little evidence of bud drop.

*Size*.—Medium, average 4.5 mm length in mid winter.

*Form*.—Plump, conic and free.

*Surface*.—Pubescent scales.

*Color*.—Brown, Stucco (Pantone 16-1412) in late summer.

Flowers:

*Blossom period*.—Blooms 5-6 days after 'Gulfcrimson' peach — average 50% bloom around February 16th most years at Attapulgus, but occurring over a 7-10 day period. Time and length of bloom are dependent on ambient temperature.

*Aroma*.—Not detectable.

*Flower density*.—Abundant, varying 1 to 3 per node, but usually 2.

*Type*.—Showy, location and seasonally variable within the range of commercial showy varieties. Average flower diameter — 4 cm. Average petal length, 20 mm; width, 14 mm. Texture smooth. Margins are undulate and smooth.

*Color*.—Color of the upper surface of the petal is Almond Blossom (Pantone 13-2006) at flower opening, and within the pink range of standard varieties.

*Flower parts*.—Stamens and pistil size, shape and color are within the range of standard commercial varieties. There are 5 sepals and petals. Sepals average 5 mm length and 5 mm wide at attachment to calyx cup and rounded at the distal end. Sepals are green, Spinach Green (Pantone 16-0439) on the interior and red, Rose Wine (Pantone 17-1623) on the exterior with a smooth pubescent margin. Sepals are pubescent and petals are glabrous. Pistils are usually 1 per flower and straight (without curls or curves) just prior to flower opening. Pistil length (from tip of stigma to base of ovary) averages 16 mm. Pistils are light green, Pale Star (Pantone 12-0626). Flower pedicel is 2 mm length.

*Calyx cup*.—Medium large in the size range of commercial varieties. Calyx cup diameter is 5 mm at the top, at the time of flower opening. Calyx cup exterior is red, Garnet (Pantone 19-1655) and interior of the cup base is cream, Vanilla (Pantone 12-0712).

*Stamen*.—Anthers are deep yellow, Apricot Orange (Pantone 17-1353), at flower opening. Number of anthers varies from 35 to 37 and filament length is 10 to 14 mm. Filaments are pink, Almond Blossom (Pantone 14-2307) at flower opening.

*Pollen*.—Abundant and yellow, Snapdragon (Pantone 13-0840).

*Fertility*.—Fully self fertile, and no cross pollination is required. Fruit set is abundant.

Fruit:

*Maturity when described*.—Tree ripe, Jun. 22, 2010 at Attapulgus, Ga.

*Date of picking*.—First, Jun. 15, 2010; Last, — Jun. 22, 2010 at Attapulgus, Ga.

*Size*.—Uniform, large (especially for early mid-season maturity) averaging 185 g over the 7 years of observation since its selection in 2006. Varies with fruit number per tree, soil type, climatic conditions and cultural practices. Average equatorial diameter.—2½ inches (63 mm). Average polar length (stem to distal end).—2⅝ inches (67 mm).

*Pedicel size and color*.—Length averages 7 mm; Width is approximately 3 mm. Color is green, Cedar (Pantone 16-0526).

*Longitudinal section form*.—Nearly round.

*Transverse section through diameter*.—Nearly round with slight suture bulge.

*Suture*.—A slight suture bulge exists from the distal to the base end of the fruit.

*Ventral surface*.—Usually rounded.

*Base*.—Slightly cordate.

*Apex*.—Usually rounded to slightly obtuse.

*Crater at stem attachment*.—Flaring circular with slight suture crease at the stem end. Depth is 9 to 10 mm; breadth is 20 mm at top and 4 mm at pedicel attachment.

*Skin*.—Thickness.—Medium in comparison to commercial peach varieties. Texture.—Medium in comparison to standard varieties. Tenacity.—Tenacious to flesh. Color.—Red, Poinsettia (Pantone 17-1654), over 50 to 60% of . Ground color is cream, Dawn (Pantone 12-0811). Fruit exposed to sunlight have a higher degree of enhanced red . Tendency to crack.—None observed. Taste.—No astringency observed. Epidermis.—Pubescent.

*Flesh*.—Ripens.—Evenly within each fruit. Texture.—Firm, but juicy and non-melting when fully ripe. Fibers.—Very fine, small, tender, and abundant. Aroma.—Moderate and in the middle range of commercial peach varieties. Eating quality.—Good, moderately sweet, slightly acid. Soluble solids average 10.6 brix and 1.7 kg penetrometer firmness with a standard 5/16 inch tip following a seven day post-harvest storage protocol. Juice.—Abundant. Color.—Cream, Vanilla (Pantone 12-0712), with red in the flesh, Poinsettia (Pantone 17-1654) and darker red at the pit. Browning by oxidation.—Very slight on cut fruit when tree ripe and beginning to soften. Amygdalin.—Undetected. Texture.—Smooth, and similar to 'Gulfcrimson'.

*Stone*.—Type.—Clingstone. Size.—Medium small: average length is 32 mm; average width is 23 mm; average thickness is 16 mm; average wall thickness is 5 mm. Color.—Red, Barn Red (Pantone 18-1531) when flesh is freshly removed.

*Form*.—Slightly oblong. Base.—Straight. Apex.—Rounded, not a sharp point. Sides.—Near equal. Surface.—Irregularly shallow pitted. Ridges.—Shallow and rounded. Tendency to split.—None observed.

*Seed*.—Bitter (amygdalin is abundant) kernel. Viable if stratified upon removal from fruit at harvest, and cultured on a germination medium. Kernel is yellow, Vanilla (Pantone 12-0712) when first removed from pit of a ripe fruit. Seed is 17 mm length, 11 mm wide and 5 mm thick. Shape is acute tip with obtuse base and overall ovate shape.

Use: Fresh; dessert.

Resistance to disease: High resistance to bacterial spot incited by *Xanthomonas campestris* pv. *pruni* (Pers.) Diet. Resistance to other fruit and tree diseases are within the range for commercial peach cultivars in Florida. No unusual resistance or susceptibility to insects and diseases noted.

Keeping quality: Excellent after 10 days at 2C and with minimal bruises or scarring appear on .

Shipping quality: Degree of firmness at harvest and firmness retained in refrigeration for 10 days at 2C, with no internal breakdown of flesh or appreciable loss of eating quality, indicates fruit should be highly acceptable for shipping.

We claim:

1. A new and distinct peach tree as illustrated and described, characterized by a moderate chilling requirement, and bearing fruit having firm, white and non-melting, clingstone, and smooth textured flesh of good eating quality and an attractive, high percentage red skin.

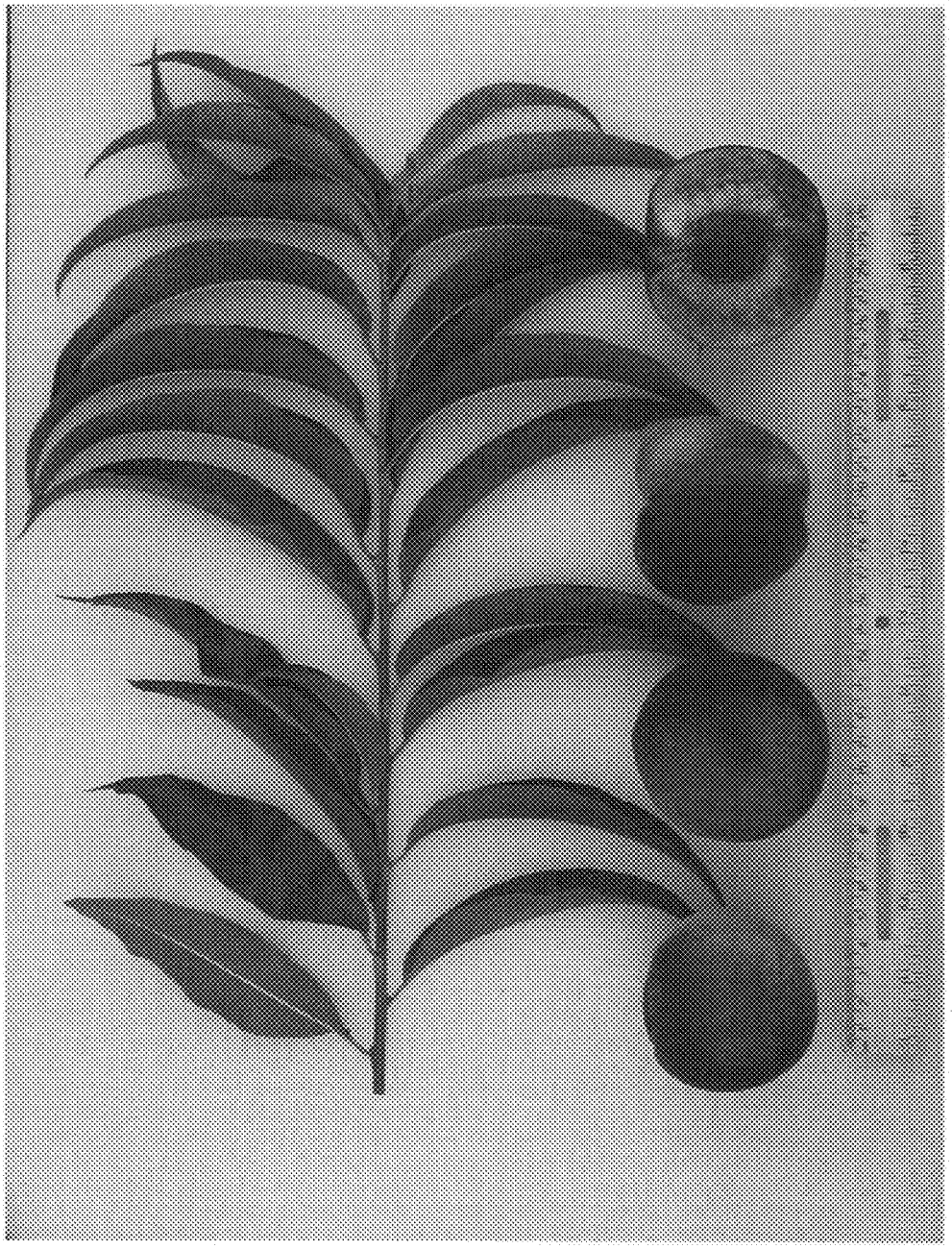

* * * * *